United States Patent [19]

Demarchez et al.

[11] Patent Number: 5,973,007
[45] Date of Patent: Oct. 26, 1999

[54] USE OF INHIBITORS OF RETINOIC ACID ACTIVITY FOR WOUND HEALING

[75] Inventors: Michel Demarchez, Le Bar sur Loup; Patricia Rossio, Plas Cassier; Andre Jomard, Saint Vallier de Thiey, all of France

[73] Assignee: Centre International de Recherches Dermatologiques Galderma, Valbonne, France

[21] Appl. No.: 09/068,956

[22] PCT Filed: Sep. 17, 1997

[86] PCT No.: PCT/FR97/01641

§ 371 Date: Jul. 28, 1998

§ 102(e) Date: Jul. 28, 1998

[87] PCT Pub. No.: WO98/11886

PCT Pub. Date: Mar. 26, 1998

[30] Foreign Application Priority Data

Sep. 20, 1996 [FR] France ................................. 96 11511

[51] Int. Cl.⁶ .......................... A61K 31/19; A61K 49/00; A61K 7/00; A61K 31/07
[52] U.S. Cl. .......................... 514/568; 424/9.8; 424/401; 514/557; 514/570; 514/725; 514/928
[58] Field of Search ................................ 514/557, 568, 514/570, 725, 928; 424/401, 9.8

[56] References Cited

U.S. PATENT DOCUMENTS

| 5,808,124 | 9/1998 | Beard et al. | 556/419 |
| 5,827,500 | 10/1998 | Demarchez et al. | 424/9.1 |

FOREIGN PATENT DOCUMENTS

| 0 448 213 | 9/1991 | European Pat. Off. |
| 0 465 343 | 1/1992 | European Pat. Off. |
| 0 568 898 | 11/1993 | European Pat. Off. |
| 0 658 553 | 6/1995 | European Pat. Off. |
| 0 661 259 | 7/1995 | European Pat. Off. |
| 0 749 755 | 12/1996 | European Pat. Off. |
| 94 14777 | 7/1994 | WIPO |
| 96 30009 | 10/1996 | WIPO |

OTHER PUBLICATIONS

MacDonald et al., "Effect of retinoic acid on wound healing of laser burns to porcine retinal pigment epithelium", Can J Ophthalmol, V. 31, No. 4, pp. 175–178, 1996.

Eyrolles et al, "Retinoid anatagonists: molecular design based on the ligand superfamily concept", Med. Cell. Res., vol. 2, 1992, pp. 361–367, XP000674651.

Kaneko et al, "Retinoic antagonists", Med. Chem. Res., vol. 1, 1991, pp. 220–225, XP00674650.

McDonald et al, "Effect of retinoic acid on wound healing of laser burns to porcine retinal pigment epithelium", Can. J. Opthalmol., vol. 31, No. 4, Jun. 1996, pp. 175–178, XP000674653.

Klein, "Identification and functional separation of retinoic acid receptor neutral antagonists and inverse agonists", J. Biol. Chem., vol. 271, No. 37, Sep. 13, 1996, pp. 22692–22696, XP002048821.

Standeven: "Specific antagonists of retinoid toxicity in mice" Toxicol. Appl. Pharmacol., vol. 138, No. 1, May 1906, pp. 169–173, XP002048822.

*Primary Examiner*—Jose' G. Dees
*Assistant Examiner*—Marina Lamm
*Attorney, Agent, or Firm*—Burns, Doane, Swecker & Mathis, L.L.P.

[57] ABSTRACT

A method for promoting healing by administration of an inhibitor of the activity of retinoic acid is provided. Preferred compounds for use in such treatment include antagonists of retinoic acid. The method is particularly applicable for promoting skin healing and treatment of surgical and traumatic wounds.

12 Claims, No Drawings

USE OF INHIBITORS OF RETINOIC ACID ACTIVITY FOR WOUND HEALING

The present invention relates to the use of inhibitors of the activity of retinoic acid to promote healing, especially of the skin.

It is known, in general, that all-trans-retinoic acid acts on the differentiation and/or the proliferation of cells by interacting with nuclear receptors of RARs (retinoic acid receptors) contained in the cell nucleus. Numerous synthetic structural analogues of all-trans-retinoic acid or of 9-cis-retinoic acid, commonly called "retinoids", have been described so far in the literature. There are so far three identified sub-types of RAR receptors called α-RAR, β-RAR and γ-RAR respectively. These receptors, after binding of the ligand (i.e. of all-trans-retinoic acid), interact with the promoter region of genes regulated by retinoic acid at the level of specific response elements (RARE).

Some analogues can therefore bind and activate a particular RAR (α, β or γ) receptor sub-type. Finally, other analogues exhibit no particular selective activity towards these various receptors. To this end, and for example, all-trans-retinoic acid activates the RARs (RAR specific agonist ligand), all sub-types taken into consideration.

Retinoic acid and retinoids in general have been claimed for treating the following disorders or conditions: acne vulgaris, comedo-type acne, polymorphic acne, acne rosacea, nodulocystic acne, acne conglobata, senile acne, secondary acne such as solar acne, acne medicamentosa or occupational acne; other keratinization disorders, in particular ichthyosis, ichthyosiform states, Darrier's disease, keratosis palmaris et plantaris, leucoplakia and leucoplakia-like states, skin or mucosal (buccal) lichen; other dermatological conditions linked to a keratinization disorder with an inflammatory and/or immunoallergic component and in particular all forms of psoriasis whether cutaneous, mucosal or ungual, and even psoriatic rheumatism, or alternatively skin atopy, such as eczema or respiratory atopy or alternatively gingival hypertrophy; certain inflammatory conditions not exhibiting keratinization disorder, such as arthritis, dermal or epidermal proliferations whether benign or malignant, whether they are of viral origin or otherwise, such as verruca vulgaris, verruca plana and epidermodysplasia verruciformis, oral and florid papillomatosis and proliferations which may be induced by ultraviolet radiation especially in the case of baso- and spinocellular epitheliomas; other dermatological disorders such as bullous dermatoses and collagen diseases; certain ophthalmological disorders, especially corneopathies; skin ageing, whether photoinduced or chronologic or actinic keratoses and pigmentations or any pathology associated with chronologic or actinic ageing; the stigmas of epidermal and/or dermal atrophy induced by local or systemic corticosteroids, or any other form of skin atrophy; healing disorders or vibices; disorders of sebaceous function such as hyperseborrhoea of acne or simple seborrhoea; cancerous or precancerous states; conditions of viral origin at the cutaneous or general level (human immunodeficiency virus: HIV-1 or hepatitis B virus); alopecia; conditions of the cardiovascular system such as arteriosclerosis.

Retinoic acid and retinoids in general, by binding with the RAR receptors, make it possible to regulate the activity of the RAR receptors and to treat the above disorders or conditions.

The antagonists of retinoic acid will, on the contrary, inhibit the activity of retinoic acid or its metabolites at the cellular level. These are more particularly the RAR antagonists which bind to the RAR receptors, but do not induce the activity observed for retinoic acid or the retinoids.

Thus, it has been shown that antagonists of the α-RAR receptors inhibit the cellular differentiation induced by the retinoids on cells of the HL60 cell line or, on the contrary, reverse the inhibition of the proliferation of mouse B cells which is induced by the retinoids (C. Apfel & al., Proc. Natl. Acad. Sci. USA, 89, 1992, 7129–7133).

Various antagonists of retinoic acid are described in patent application EP 568 898. They are recommended for treating the problems of overregulation of the RAR receptors, in particular immunological conditions, autoimmune conditions or conditions having a strong immunological component, such as psoriasis.

The harmful effect of a vitamin A deficiency on skin healing was described by Reed & Clark in 1985 (B. R. Reed & R. A. F. Clark, J. Am. Acad. Dermatol. 13, 6, 1985, 919–941).

The need for retinoic acid in the normal development of the skin has been confirmed by the expression of a retinoic acid dominant-negative receptor in mice (M. Saitou, Nature, 374, 1995, 159). It was shown that the deficiency in retinoic acid activity caused inhibition of the development of the skin with suppression of the maturation of the epidermis.

Given this need and the knowledge on the activity of the retinoids and of the antagonists, it could therefore be assumed that these retinoic acid antagonists, by inhibiting its activity at the cellular level, could treat healing disorders by slowing it down, whereas retinoids would accelerate it.

Indeed, healing, more particularly skin healing, is a complex process in which the various dermal and/or epidermal events are closely linked, and comprise the following different phases: formation of a crust, production of a granulation tissue and coming together of the edges of the wound, and formation of an epidermis and then of a neodermis.

When a dermo-epidermal wound is induced, there is a first inflammatory phase whose major role is to clean the wound with formation of a crust which separates it from the external medium.

Under this crust will then develop a granulation tissue essentially consisting of blood vessels and of specialized fibroblasts called "myofibroblasts". They are cells which will participate in the phenomenon retraction of the wound which has the role of bringing together the edges of the wound.

Between the crust and the granulation tissue, on the latter, the keratinocytes derived from the edges of the wound will migrate to reform an epidermis: this is the phenomenon of reepithelialization.

Under the reconstructed epidermis, the granulation tissue has passed from a cellular state (rich in cells) to a fibrous state (rich in extracellular matrix). Subsequently, this fibrous scar tissue is invaded by fibroblasts derived from uninjured peripheral dermis which will reconstruct the neodermis.

The retraction of the wound is not a necessary step in healing. Its essential role is to reduce the space to be "reepidermized" between the edges of the wound. In some cases, this retraction of the wound can be the cause of major disorders by inducing losses of function, especially near orifices or joints, for example in the case of hand burns.

It is therefore important to be able to have new compounds which make it possible to promote healing, in particular skin healing, that is to say which promote reepidermization (reepithelialization and normalization of the epidermis and of the dermis) and/or which limit the phenomenon of retraction of the wound.

Now, contrary to what could be expected given the knowledge on the need for retinoic acid for the maturation of the epidermis and the growth of the skin, we have now been able to demonstrate the fact that the inhibition of the activity of retinoic acid or of its metabolites, and more particularly of the activity of endogenous retinoic acid, makes it possible to promote healing, whereas the retinoids, by reinforcing the activity of endogenous retinoic acid, slow down the closing of the wound. This observation is all the more remarkable since it was made on normal skins, that is to say which do not exhibit healing disorders which might have been linked to an A hypervitaminosis.

The present invention therefore relates to the use of at least one inhibitor of the activity of retinoic acid in a cosmetic composition or for the preparation of a pharmaceutical composition, the inhibitor of the activity of retinoic acid or the pharmaceutical composition being intended to promote healing, in particular skin healing.

The inhibitors of the activity of retinoic acid can act according to two pathways, the first by accelerating the cellular metabolism of retinoic acid so as to reduce the cellular concentration of the latter, the second by antagonizing its action at the cellular level.

The inhibitors of the activity of retinoic acid can therefore be, according to the invention, accelerators of the metabolism of retinoic acid or antagonists, reverse agonists or partial agonists of retinoic acid.

By antagonists of retinoic acid, there is preferably understood according to the invention the compounds which inhibit the action of retinoic acid and/or of its metabolites and/or of the retinoids. They are more particularly RAR antagonists which bind to the RAR receptors without, however, activating them.

There is understood more particularly the compounds which inhibit the activity of retinoic acid "in vivo" selected according to the test described in patent application EP 96 401 170 filed on May 31, 1996 in the name of Cird Galderma. This is a process for identifying molecules which are RAR antagonists, characterized in that it comprises the following stages: (i) a sufficient quantity of a molecule which is an RAR agonist is applied topically to a part of the skin of a mammal, (ii) a molecule capable of having an antagonist activity for the RARs is administered by the systemic or topical route to this same mammal or to this same part of the skin of the mammal, before, during or after stage (i), and (iii) the response on the part of the mammalian skin thus treated is evaluated. Thus, when the administered molecule is an antagonist of the RARs, the increase in the thickness of that part of the mammalian skin treated with an agonist molecule for the RARs is not observed or is reduced. An inhibition of the response is therefore observed. In practice, the mammal is a rodent such as a mouse, a rat, a guinea pig, a hamster or a rabbit. The part of the mammalian skin used may be any part of the mammal's body. The response on the thus treated part of the mammalian skin which is to be evaluated corresponds to a clinical modification of the said skin part. In general, this response to be evaluated corresponds to a modification of the thickness of the part of the skin thus treated. The measurement of the thickness of the part of the skin thus treated can be performed by any method known per se. When the part of the skin used is smooth, it is possible to measure its thickness by folding it. More practically, the skin of the ear is used. The measurement of the thickness of the ear can then be carried out by an "oditest" micrometer. Of course, the evaluation of stage (iii) corresponds to a measurement of the response of the part of the skin thus treated and to a comparison of this measurement with that of the response of this same part of the skin treated, under the same conditions, with the agonist molecule for the RARs on its own. Preferably, the agonist molecules for the RARs are chosen among the compounds capable of inducing the differentiation of mouse embryonic teratocarcinoma cells (F9). The secretion of plasminogen activator which accompanies this differentiation is an indication of the biological response of the F9 cells to these compounds. It is also known that the capacity of these compounds to induce plasminogen activator is directly correlated with the affinity and the activity which they have on the RAR receptors which are endogenous to the F9 cells (Skin Pharmacol., 1990, 3, pp. 256–267). Among the agonist molecules for the RARs which induce the differentiation of the F9 cells, there may be mentioned more particularly:

all-trans-retinoic acid, 2-(5,6,7,8-tetrahydro-5,5,8,8-tetramethyl-2-naphthyl)-6-benzo[b]thiophenecarboxylic acid, 4-[(5,6,7,8-tetrahydro-5,5,8,8-tetramethyl-2-naphthyl)carboxamido]benzoic acid, 4-[(5,6,7,8-tetrahydro-5,5,8,8-tetramethyl-2-naphthyl)carbamoyl]benzoic acid.

In the text which follows or in the preceding text, topical route is understood to mean any technique for administering a product by direct application thereof to a superficial (or external) part of the body, and systemic route is understood to mean any technique for administering a product by a route other than the topical route, for example the enteral and parenteral route. In the case of the systemic route, the use of the oral route is preferred. The sufficient quantity of an agonist molecule for the RARs to be applied corresponds to that at which a response of the treated part of the skin of the mammal is observed after stage (i). Thus, preferably and depending on the nature of the agonist molecule for the RARs which is used, this quantity varies between 0.0001% and 2% by weight per volume of solution applied.

The antagonists of retinoic acid are in particular the compounds described in patent applications EP 661 259, EP 740 937, EP 658 553, EP 568 898, WO 95/33745, WO 97/09297 and WO 94/14777, and in several scientific publications, in particular Eyrolles & al. (J. Med. Chem., 37, 1994, 1508–1517; Med. Chem. Res., 2, 1992, 361–367) and Kaneko & al. (Med. Chem. Res., 1, 1991, 220–225) which inhibit the action of retinoic acid and/or of the retinoids.

The RAR antagonists of use according to the invention are in particular selected from the following compounds:

4-[7-(1-adamantyl)-6-methoxyethoxymethoxy-2-naphthyl]benzoic acid,

4-{[5,6-dihydro-5,5-dimethyl-8-(4-methylphenyl)-2-naphthalenyl]ethynyl}benzoic acid, (E)-4-[2-(4,4-dimethyl-7-heptyloxy-1,1-dioxo-3,4-dihydro-2H-1-benzothiopyran-6-yl)propenyl]benzoic acid, 4-[4,5,7,8,9,10-hexahydro-7,7,10,10-tetramethyl-1-(3-pyridylmethyl)anthra[1,2-b]pyrrol-3-yl]benzoic acid, 4-[4,5,7,8,9,10-hexahydro-7,7,10,10-tetramethyl-1-(3-pyridylmethyl)thioanthra[1,2-b]pyrrol-3-yl]benzoic acid, 4-[4,5,7,8,9,10-hexahydro-7,7,10,10-tetramethyl-1-(3-pyridylmethyl)anthra[1,2-d]pyrazol-3-yl]benzoic acid, 4-[3-(diamantyl)-4-methoxybenzamido]benzoic acid, 4-[3-(diamantyl)-4-methoxybenzoyloxy]benzoic acid, 4-(N-phenyl-5,6,7,8-tetrahydro-5,5,8,8-tetramethylnaphtho[2,3-d]imidazol-2-yl)benzoic acid, 4-(N-benzyl-5,6,7,8-tetrahydro-5,5,8,8-tetramethylnaphtho[2,3-d]imidazol-2-yl)benzoic acid, 4-(5H-7,8,9,10-tetrahydro-5,7,7,10,10-pentamethylbenzo[c]-naphtho[2,3-b][1,4]diazepin-3-yl)benzoic acid, 4-[1-(1-methoxy-2,2,2-trifluoroethyl)-5,6,7,8-tetrahydro-5,5,8,8-tetramethyl-3-anthracenyl]benzoic acid, 4-(5,5-dimethyl-8-phenyl-5,6-dihydronaphthalen-2-ylethynyl)benzoic acid, 4-(5,5-dimethyl-8-p-tolyl-5,6-dihydronaphthalen-2-ylethynyl)benzoic acid.

Within the framework of the invention, the inhibitors of the activity of retinoic acid can be advantageously used in combination with other active compounds, in particular which are useful for promoting healing, which do not counteract the activity of the inhibitor of the activity of retinoic acid for promoting healing. They are in particular compounds such as vitamin C, vitamin K, vitamin B, vitamin E or mixtures thereof; disinfectants; antibiotics administered by the topical or systemic route such as erythromycin and its esters, neomycin, gentamycin, clindamycin and its esters, tetracyclines, antifungal agents such as ketoconazole or 4,5-polymethylene-3-isothiazolidones; topical antimicrobial agents, in particular iodophors, complexes or salts of silver, copper or zinc, benzoyl peroxide, extracts of Aloe vera; growth factors; sphingosylphosphorylcholine, and the like.

In this case, the inhibitor of the activity of retinoic acid and the other active compounds can be administered together in the same cosmetic or pharmaceutical composition, or separately in separate compositions, simultaneously or spaced out over time.

The cosmetic or pharmaceutical composition comprising at least one inhibitor of the activity of retinoic acid comprises a cosmetically or pharmaceutically acceptable carrier compatible with the mode of administration selected.

The quantity of inhibitor of the activity of retinoic acid is an effective quantity depending of course on the desired treatment and the nature of chosen compound; it is therefore determined by persons skilled in the art.

The administration of the compounds according to the invention may be carried out by the systemic (especially enteral or parenteral), topical or ocular route.

By the enteral route, the composition is more particularly a pharmaceutical composition which may be provided in the form of tablets, gelatine capsules, sugar-coated tablets, syrups, suspensions, solutions, powders, granules, emulsions, lipid or polymeric microspheres or nanospheres or vesicles which allow a controlled release. By the parenteral route, the composition, more particularly the pharmaceutical composition, may be provided in the form of solutions, emulsions or suspensions for infusion or for injection.

The inhibitors of the activity of retinoic acid, more particularly the antagonists of retinoic acid are generally administered in a daily dose of about 0.01 mg/kg to 100 mg/kg as body weight, and this at the rate of 1 to 3 doses.

By the topical route, the composition is a cosmetic or pharmaceutical composition, more particularly intended for the treatment of the skin and/or of the mucous membranes. It can therefore be provided in the form of solutions or suspensions, ointments, pommades, creams, milks, gels, powders, impregnated pads, lotions, sprays, or foaming or cleansing products. It can also be provided in the form of lipid or polymeric microspheres or nanospheres or vesicles or of polymeric patches, hydrogels or dressings allowing a controlled release. This composition for the topical route can, moreover, be provided either in anhydrous form or in an aqueous form.

The topical composition may also comprise appropriate excipients for forming a film at the surface of the skin, either to isolate the wound to be healed from the external medium or to avoid contaminations, or for forming a hydrophobic matrix which attracts, by osmosis, fluids, bacteria and tissue debris.

By the ocular route, the composition may in this case be provided in the form of ointments, creams, gels or collyria which are appropriate for this specific application.

This composition for topical or ocular use contains at least one antagonist of retinoic acid at a concentration preferably of between 0.001% and 5% by weight relative to the total weight of the composition.

The composition according to the invention may, in addition, contain inert or even pharmacodynamically or cosmetically active additives or combinations of these additives, and in particular wetting agents; emollients; moisturizing agents such as glycerol, PEG 400, thiamorpholinone and its derivatives or alternatively urea; non-steroidal anti-inflammatory agents; carotenoids and, in particular, β-caroten.

The composition may also contain taste-enhancing agents, preservatives such as esters of parahydroxybenzoic acid, stabilizing agents, humidity-regulating agents, pH-regulating agents, osmotic pressure-modifying agents, emulsifying agents, UV-A and UV-B screening agents, hydrophilic or lipophilic antioxidants, such as α-tocopherol, butylated hydroxyanisole or butylated hydroxytoluene, chelators such as EDTA and its salts.

The compositions according to the invention are particularly useful for improving healing, in particular for the treatment of surgical wounds, especially wounds induced by plastic surgery and/or by the peelings obtained by the chemical (acid) route, by dermoabrasion or by laser, and/or traumatic wounds, in particular cuts or burns of all sorts, such as the burns induced by UV radiation.

The examples below make it possible to illustrate the invention without, however, seeking to limit its scope.

EXAMPLE 1

Study of the Activity of the Antagonists of Retinoic Acid on Healing

This example is intended to demonstrate the activity of an RAR antagonist in the process of healing of an experimentally induced skin wound.

Method

The studies are carried out on human skin transplanted onto nude mice according to the method described by Demarchez & al. (M. Demarchez & al., Develop. Biology, 113, 1986, 90–96; M. Demarchez & al., Develop. Biology, 121, 1987, 119–129).

A deep wound is made on the human skin transplanted onto nude mice by cutting away the skin at the centre of the graft with the aid of a 2 mm punch. The wound is then left in the open air.

4-[7-(1-Adamantyl)-6-methoxyethoxymethoxy-2-naphthyl]benzoic acid (RAR antagonist) in suspension in 25% cremophor EL at the dose of 30 mg/kg (product tested), or the vehicle alone (control), is administered per os by gavage in a volume of 10 mg/kg.

The treatment is administered once per day for 7 days starting from the day the skin wound is induced (immediate treatment) in 8 mice (4 in the test product group and 4 in the control group) and once per day for 7 days starting 7 days after induction of the skin wound (differed treatment) in 10 mice (5 in the test product group and 5 in the control group).

24 hours after the last treatment, the mice are anaesthetized and the insensitive loss of water (ilw) is measured at the level of the graft and then the mice are subjected to euthanasia. The grafts are cut at the limit of the scar zone and frozen in liquid nitrogen.

The samples are cut in a cryostat at 5 μm so as to obtain serial sections on the entire wound region.

A hemalum-eosin-saffron staining is performed for the histological examination of the scar zone. Labellings with the aid of antibodies according to the immunofluorescence method are performed for studying the healing process in the dermis and in the epidermis at various levels of the wound zone. The following antibodies are used: anti-human involucrin (epidermal differentiation), AE1 (keratins of the basal layer), anti-keratin K10, anti-human vimentin (cells of mesenchymatous origin of the dermis and of the epidermis), TMH1 (melanocytes), anti-HLADR (Langerhans' cells), anti-factor VIII (blood vessels), anti-collagen IV (collagen of the basal membranes).

The measurements and observations carried out on the group treated with 4-[7-(1-adamantyl)-6-methoxyethoxymethoxy-2-naphthyl]benzoic acid are expressed relative to the measurements and observations carried out on the control group (treated with the vehicle).

Results

Immediate treatment: After 7 administrations by the oral route in the model for healing of the human skin transplanted onto nude mice, starting the treatment on the day the wound is induced, 4-[7-(1-adamantyl)-6-methoxyethoxymethoxy-2-naphthyl)benzoic acid does not modify the i.l.w. in a statistically significant manner and does not induce morphological modification at the level of the uninjured zone of the graft, but it normalizes the epidermal differentiation and stimulates the reappearance of the Langerhans' cells in the zones at the edge of the graft and at the edge of the wound.

In the injured zone, a more advanced progression of the epidermal tongues, an improved differentiation, the presence of melanocytes and of Langerhans' cells at the periphery, a more developed connective tissue and a decrease in the retraction of the wound are observed.

These data indicate that 4-[7-(1-adamantyl)-6-methoxyethoxymethoxy-2-naphthyl]benzoic acid promotes the reconstruction of the dermal and epidermal tissues. Differed treatment: After 7 administrations by the oral route, 4-[7-(1-adamantyl)-6-methoxyethoxymethoxy-2-naphthyl] benzoic acid in the model for healing of the human skin transplanted onto nude mice, starting the treatment 7 days after inducing the wound, the morphological study shows that the wound is completely reepithelialized and that it has not retracted. Normalization of the differentiation of the epidermis from the edges of the wound and a good cohesion of the dermo-epidermal junction are observed.

These results show clearly that the inhibitors of the activity of retinoic acid or of its metabolites, and more particularly the RAR antagonists promote reepithelialization of a skin wound and by its pro-differentiating activity, accelerates the normalization of the epidermis reconstructed, while limiting the phenomenon of retraction of the wound.

EXAMPLE 2

Compositions

The compositions below are examples of compositions capable of being used to apply or administer antagonists of retinoic acid for the purpose of promoting healing.

A - ORAL ROUTE (a) Immediate release 0.2 g tablet (granulation)

| | |
|---|---|
| Antagonist of retinoic acid | 0.0010 g |
| Lactose codex | 0.1204 g |
| Microcrystalline cellulose (Avicel PH 101) | 0.0640 g |
| Polyvinylpyrrolidone (Kollidon K30) | 0.0060 g |
| Colloidal silica (Aerosil 200) | 0.0006 g |
| Magnesium stearate | 0.0020 g |
| Sodium starch glycolate (Explotab) | 0.0060 g |
| Purified water qs granulation | |

(b) Immediate-release 0.8 g tablet (direct compression)

| | |
|---|---|
| Antagonist of retinoic acid | 0.0800 g |
| Modified starch (Starch 1500) | 0.2984 g |
| Microcrystalline cellulose (Avicel PH 102) | 0.4000 g |
| Colloidal silica (Aerosil 200) | 0.0016 g |
| Magnesium stearate | 0.0040 g |
| Sodium Croscarmellose (Ac-Di-Sol) | 0.0160 g |

(c) 0.2 g gelatin capsule (soft capsule or hard gelatin capsule filled with liquid)

| | |
|---|---|
| Antagonist of retinoic acid | 0.0050 g |
| Unsaturated polyglycosylated glycerides or vegetable oil (soyabean, maize and the like) | 0.1845 g |
| White beeswax or hydrogenated castor oil | 0.0100 g |
| BHT | 0.0001 g |
| dl-α-tocopherol | 0.0004 g |

(d) Oral solution in 5 ml vials

| | |
|---|---|
| Antagonist of retinoic acid | 0.0001 g |
| Glycerol | 0.7500 g |
| Sorbitol | 1.0000 g |
| Propylene glycol | 1.0000 g |
| Polyvinylpyrrolidone (Kollidon K25) | 0.5000 g |
| Sodium cyclamate | 0.0050 g |
| Sodium parahydroxybenzoate | 0.0040 g |
| Flavouring qs | |
| Purified water qs | 5 ml |

B - TOPICAL ROUTE (a) Ointment

| | |
|---|---|
| Antagonist of retinoic acid | 0.020 g |
| Isopropyl myristate | 81.700 g |
| Fluid petroleum jelly | 9.100 g |
| Silica ("Aerosil 200" sold by Degussa) | 9.180 g |

(b) Ointment

| | |
|---|---|
| Antagonist of retinoic acid | 0.300 g |
| Petroleum jelly codex qs | 100 g |

(c) Non-ionic water-in-oil cream

| | |
|---|---|
| Antagonist of retinoic acid | 0.100 g |
| Mixture of emulsifying lanolin alcohols, of waxes and of oils ("Eucerine anhydre" sold by BDF) | 39.900 g |
| Methyl para-hydroxybenzoate | 0.075 g |
| Propyl para-hydroxybenzoate | 0.075 g |
| Sterile demineralized water qs | 100 g |

(d) Lotion

| | |
|---|---|
| Antagonist of retinoic acid | 0.100 g |
| Polyethylene glycol (PEG 400) | 69.900 g |
| Ethanol 95% | 30.000 g |

(e) Non-ionic oil-in-water cream

| | |
|---|---|
| Antagonist of retinoic acid | 1.000 g |
| Cetyl alcohol | 4.000 g |
| Glycerol monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water qs | 100 g |

We claim:

1. A method for promoting the healing of normal skin, said method comprising administering an effective amount of an inhibitor of the activity of retinoic acid to a patient is need of such treatment.

2. The method according to claim 1, wherein the inhibitor of the activity of retinoic acid is an antagonist of retinoic acid.

3. The method according to claim 2, wherein the antagonist of retinoic acid is identified by a process comprising the following stages: (i) a sufficient quantity of a molecule which is an RAR agonist is applied topically to a part of the skin of a mammal, (ii) a molecule capable of having an antagonist activity for the RARs is administered by the systemic or topical route to this same mammal or to this same part of the skin of the mammal, before, during or after stage (i), and (iii) the response on the part of the mammalian skin thus treated is evaluated.

4. The method according to claim 2, wherein the antagonists of retinoic acid are selected from the following compounds:

4-[7-(1-adamantyl)-6-methoxyethoxymethoxy-2-naphthyl]benzoic acid,

4-{[5,6-dihydro-5,5-dimethyl-8-(4-methylphenyl)-2-naphthalenyl]ethynyl}benzoic acid, (E)-4-(2-(4,4-dimethyl-7-heptyloxy-1,1-dioxo-3,4-dihydro-2H-1-benzothiopyran-6-yl)propenyl]benzoic acid, 4-[4,5,7,8,9,10-hexahydro-7,7,10,10-tetramethyl-1-(3-pyridylmethyl)anthra[1,2-b] pyrrol-3-yl]benzoic acid, 4-[4,5,7,8,9,10-hexahydro-7,7,10,10-tetramethyl-1-(3-pyridylmethyl)thioanthra[1,2-b]pyrrol-3-yl]benzoic acid, 4-[4,5,7,8,9,10-hexahydro-7,7,10,10-tetramethyl-1-(3-pyridylmethyl)anthra[1,2-d]pyrazol-3-yllbenzoic acid, 4-[3-(diamantyl)-4-methoxybenzamido]benzoic acid, 4-[3-(diamantyl)-4-methoxybenzoyloxylbenzoic acid, 4-(N-phenyl-5,6,7,8-tetrahydro-5,5,8,8-tetramethylnaphtho[2,3-dlimidazol-2-yl)benzoic acid, 4-(N-benzyl-5,6,7,8-tetrahydro-5,5,8,8-tetramethylnaphtho[2,3-d]imidazol-2-yl)benzoic acid, 4-(5H-7,8,9,10-tetrahydro-5,7,7,10,10-pentamethylbenzo[c]-naphtho[2,3-b][1,4]diazepin-3-yl)benzoic acid, 4-[1-(1-methoxy-2,2,2-trifluoroethyl)-5,6,7,8-tetrahydro-5,5,8,8-tetramethyl-3-anthracenyl]benzoic acid, 4-(5,5-dimethyl-8-phenyl-5,6-dihydronaphthalen-2-ylethynyl)benzoic acid, 4-(5,5-dimethyl-8-p-tolyl-5,6-dihydronaphthalen-2-ylethynyl)benzoic acid.

5. The method according to claim 1, wherein said inhibitor of the activity of retinoic acid is administered as a composition along with a pharmaceutically or cosmetically acceptable carrier therefor.

6. The method according to claim 5, wherein the cosmetic or pharmaceutical composition comprises other active compounds.

7. The method according to claim 5, wherein the composition is a pharmaceutical composition in the form of tablets, gelatin capsules, sugar-coated tablets, syrups, suspensions, solutions, powders, granules, emulsions, lipid or polymeric microspheres or nanospheres or vesicles which allow a controlled release, solutions or suspensions for infusion or for injection.

8. The method according to claim 7, wherein the inhibitors of the activity of retinoic acid are administered in a daily dose of about 0.01 mg/kg to 100 mg/kg based on body weight, and at a frequency of 1 to 3 doses per day.

9. The method according to claim 5, wherein the cosmetic or pharmaceutical composition is provided in the form of solutions or suspensions, ointments, pommades, creams, milks, gels, powders, impregnated pads, lotions, sprays, or foaming or cleansing products, in the form of lipid or polymeric microspheres or nanospheres or vesicles or of polymeric patches, hydrogels or dressings allowing a controlled release, either in anhydrous form or in aqueous form, which may also comprise appropriate excipients for forming a film at the surface of the skin.

10. The method according to claim 5, wherein the quantity of inhibitor of the activity of retinoic acid is between 0.001% and 5% by weight relative to the total weight of the composition.

11. The method according to claim 5, wherein said composition is applied topically.

12. The method according to claim 1, wherein said composition is used for the treatment of surgical or traumatic wounds.

* * * * *